(12) United States Patent
Glidden et al.

(10) Patent No.: US 12,194,187 B2
(45) Date of Patent: Jan. 14, 2025

(54) SYSTEM AND METHOD FOR AUTOMATED DETECTION AND DISINFECTION OF A FLEET OF AUTONOMOUS VEHICLES

(71) Applicant: GM Cruise Holdings LLC, San Francisco, CA (US)

(72) Inventors: Samuel Harrison Glidden, Phoenix, AZ (US); Erik Nielsen, Glendale, AZ (US); Sriram Salem Kannan, San Francisco, CA (US); Kenneth Ramon Ferguson, Scottsdale, AZ (US); Maximilian Gerrit Euchenhofer, Phoenix, AZ (US); Michael Frank Schmidt, Scottsdale, AZ (US)

(73) Assignee: GM Cruise Holdings LLC, San Francisco, CA (US)

( * ) Notice: Subject to any disclaimer, the term of this patent is extended or adjusted under 35 U.S.C. 154(b) by 0 days.

(21) Appl. No.: 18/457,163

(22) Filed: Aug. 28, 2023

(65) Prior Publication Data

US 2023/0398253 A1 Dec. 14, 2023

Related U.S. Application Data

(63) Continuation of application No. 16/991,350, filed on Aug. 12, 2020, now Pat. No. 11,771,786.

(51) Int. Cl.
*A61L 2/00* (2006.01)
*A61L 2/18* (2006.01)
*A61L 2/22* (2006.01)
*A61L 2/24* (2006.01)
*G01C 21/34* (2006.01)

(52) U.S. Cl.
CPC ............... *A61L 2/24* (2013.01); *A61L 2/0023* (2013.01); *A61L 2/0047* (2013.01); *A61L 2/18* (2013.01); *A61L 2/22* (2013.01); *G01C 21/3407* (2013.01); *A61L 2202/11* (2013.01); *A61L 2202/14* (2013.01); *A61L 2202/15* (2013.01); *A61L 2202/25* (2013.01)

(58) Field of Classification Search
CPC .................................................. G01C 21/3407
See application file for complete search history.

(56) References Cited

U.S. PATENT DOCUMENTS

2019/0176768 A1* 6/2019 Diaz Garcia ...... B60H 1/00357
2020/0061223 A1* 2/2020 Hallack .................. B60N 2/002

FOREIGN PATENT DOCUMENTS

CN 106642524 B * 10/2019 ............... A61L 9/14
DE 102013221366 A1 * 5/2014 ......... B60H 1/00742

OTHER PUBLICATIONS

CN_106642524_B_I_Translation (Year: 2019).*
DE_102013221366_A1_translation (Year: 2019).*

* cited by examiner

*Primary Examiner* — Kevin Joyner
*Assistant Examiner* — Changru Chen (57) ABSTRACT

Systems and methods are provided for automated detection and disinfection of microbes in autonomous vehicles, to prevent possible transmission of diseases or illness to subsequent users. Automated detection and disinfection of a vehicle includes autonomously scanning various parts of the autonomous vehicle for microbes, selecting a disinfectant based on detected microbes, and autonomously disinfecting at least a portion of the autonomous vehicle.

20 Claims, 7 Drawing Sheets

SYSTEM AND METHOD FOR AUTOMATED DETECTION AND DISINFECTION OF A FLEET OF AUTONOMOUS VEHICLES

CROSS-REFERENCE TO RELATED APPLICTION(S)

This application claims the benefit of and hereby incorporates by reference, for all purposes, the entirety of the contents of U.S. Nonprovisional application Ser. No. 16/991,350 filed Aug. 12, 2020, and entitled, "SYSTEM AND METHOD FOR AUTOMATED DETECTION AND DISINFECTION OF A FLEET OF AUTONOMOUS VEHICLES".

TECHNICAL FIELD OF THE DISCLOSURE

The present disclosure relates generally to autonomous vehicle fleets and, more specifically, to methods and systems for detecting pathogens and applying disinfecting protocols in a ride service provided by an autonomous vehicle fleet.

BACKGROUND

Ridesharing services that use autonomous vehicles (AVs) to provide rides to users may help prevent the spread of disease by not exposing drivers to potentially sick passengers or exposing passengers to potentially sick drivers. However, even without a driver, an autonomous vehicle can pass diseases from sick passengers to healthy passengers. Viruses or bacteria shed by a sick passenger can linger on surfaces of the autonomous vehicle, such as door handles or arm rests, and in the air inside the autonomous vehicle. These lingering pathogens pose a risk to other passengers who ride in the autonomous vehicle, even if the sick and healthy passengers do not ride in the autonomous vehicle at the same time. Other services provided by autonomous vehicle fleets can create similar risks. For example, if a sick person loads an item for delivery into a compartment of the autonomous vehicle, the delivery item, and portions of the autonomous vehicle that the person came into contact with, may be contaminated, which exposes the recipient of the delivery item and other users of the autonomous vehicle to disease.

SUMMARY

Systems and methods are provided for automated detection and disinfection of microbes in autonomous vehicles, to prevent possible transmission of diseases or illness to subsequent users. Automated detection and disinfection of a vehicle includes autonomously scanning various parts of the autonomous vehicle for microbes, selecting a disinfectant based on detected microbes, and autonomously disinfecting at least a portion of the autonomous vehicle.

According to one aspect, a method for automated detection and disinfection of microbes in an autonomous vehicle includes autonomously scanning a plurality of identified parts of the autonomous vehicle for microbes, detecting microbes on at least one of the plurality of parts, selecting an automatic disinfecting method based on the microbes, and autonomously disinfecting at least one of the identified parts of the autonomous vehicle, wherein the at least one part includes the microbes.

According to another aspect, a system for automated detection and disinfection of microbes in an autonomous vehicle, includes a microbe detection unit, an onboard computer, and a disinfection system. The microbe detection unit is configured to autonomously perform microbe detection and includes a scanning element configured to scan a plurality of identified parts of the autonomous vehicle for microbes. The onboard computer is configured to receive scans from the scanning element, and determine whether microbes are detected on each of the plurality of parts. The disinfection system is configured to autonomously disinfect the plurality of parts of the autonomous vehicle.

According to another aspect, a method for automated identification and disinfection of microbes in an autonomous vehicle includes autonomously detecting a plurality of microbes on a part of the autonomous vehicle, identifying a species of the plurality of microbes, selecting a disinfectant based on the species of the plurality of microbes, and autonomously disinfecting at least the part of the autonomous vehicle using the selected disinfectant.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

The systems, methods and devices of this disclosure each have several innovative aspects, no single one of which is solely responsible for all of the desirable attributes disclosed herein. Details of one or more implementations of the subject matter described in this specification are set forth in the description below and the accompanying drawings.

Services that rely on shared vehicles, such as autonomous vehicle-enabled ride or delivery services, can lead to transmission of disease between users who come into contact with the same vehicle. For example, some pathogens, like measles and influenza viruses, can remain airborne for an extended period of time, and a healthy rider who enters an autonomous vehicle after a sick rider has exited the autonomous vehicle may catch the disease from the contaminated air. Additionally, some pathogens, such as the severe acute respiratory syndrome coronavirus 2 (SARS-CoV-2) and noroviruses, can survive on surfaces and be passed to other users who touch the surface; this process is referred to as fomite transmission. The risk to users is especially high during times of high rates of disease, such as during an epidemic or a pandemic.

Systems and methods are provided for automated detection and disinfection of microbes in an autonomous vehicle, including autonomously scanning various parts of the autonomous vehicle for microbes, selecting a disinfectant based on detected microbes, and autonomously disinfecting at least a portion of the autonomous vehicle.

Example Autonomous Vehicle Configured to Detect Microbes and Disinfect

Figure 1:
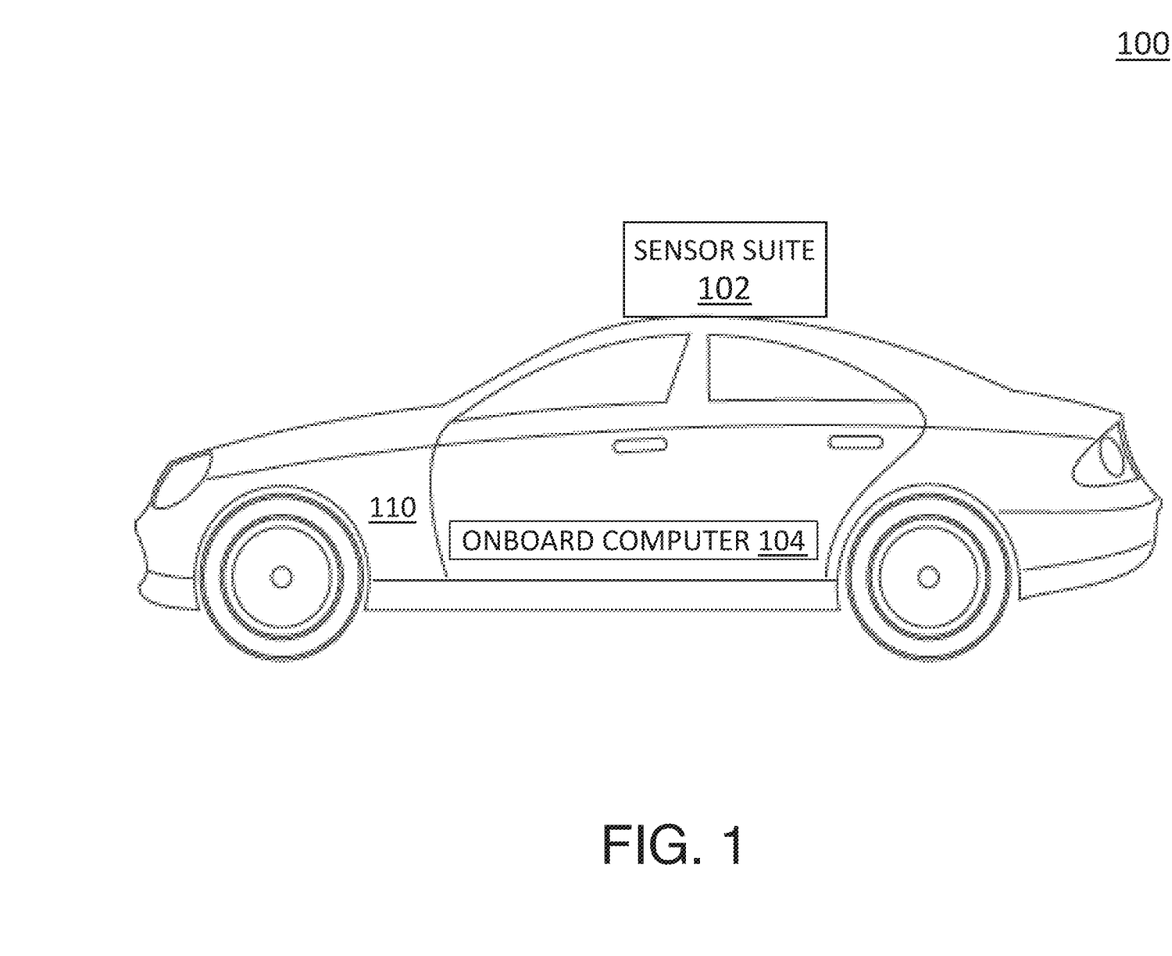
FIG. 1 is a diagram illustrating an autonomous vehicle 110 equipped for microbe detection and disinfection, according to some embodiments of the present disclosure.

FIG. 1 is a diagram 100 illustrating an autonomous vehicle 110 equipped for microbe detection and disinfection, according to some embodiments of the disclosure. The autonomous vehicle 110 includes a sensor suite 102 and an onboard computer 104. In various implementations, the autonomous vehicle 110 uses sensor information from the sensor suite 102 to determine its location, to navigate traffic, and to sense and avoid obstacles. According to various implementations, the autonomous vehicle 110 is part of a fleet of vehicles for picking up passengers and/or packages and driving to selected destinations.

The sensor suite 102 includes localization and driving sensors. For example, the sensor suite may include one or more of photodetectors, cameras, RADAR, SONAR, LIDAR, GPS, inertial measurement units (IMUs), accelerometers, microphones, strain gauges, pressure monitors, barometers, thermometers, altimeters, wheel speed sensors, and a computer vision system. The sensor suite 102 continuously monitors the autonomous vehicle's environment and, in some examples, sensor suite 102 data is used to detect selected events, and update a high fidelity map.

In various examples, the sensor suite 102 includes cameras implemented using high-resolution imagers with fixed mounting and field of view. In further examples, the sensor suite 102 includes LIDARs implemented using scanning LIDARs. Scanning LIDARs have a dynamically configurable field of view that provides a point-cloud of the region intended to scan. In still further examples, the sensor suite 102 includes RADARs implemented using scanning RADARs with dynamically configurable field of view.

The autonomous vehicle 110 includes an onboard computer 104, which functions to control the autonomous vehicle 110. The onboard computer 104 processes sensed data from the sensor suite 102 and/or other sensors, in order to determine a state of the autonomous vehicle 110. In some implementations described herein, the autonomous vehicle 110 includes sensors inside the vehicle. In some examples, the autonomous vehicle 110 includes one or more cameras inside the vehicle. The cameras can be used to detect items or people inside the vehicle. In some examples, the autonomous vehicle 110 includes one or more weight sensors inside the vehicle, which can be used to detect items or people inside the vehicle. In some examples, the interior sensors can be used to detect passenger body temperature and selected passenger behaviors such as coughing and sneezing. Based upon the vehicle state and programmed instructions, the onboard computer 104 controls and/or modifies driving behavior of the autonomous vehicle 110.

The onboard computer 104 functions to control the operations and functionality of the autonomous vehicle 110 and processes sensed data from the sensor suite 102 and/or other sensors in order to determine states of the autonomous vehicle. In some implementations, the onboard computer 104 is a general-purpose computer adapted for I/O communication with vehicle control systems and sensor systems. In some implementations, the onboard computer 104 is any suitable computing device. In some implementations, the onboard computer 104 is connected to the Internet via a wireless connection (e.g., via a cellular data connection). In some examples, the onboard computer 104 is coupled to any number of wireless or wired communication systems. In some examples, the onboard computer 104 is coupled to one or more communication systems via a mesh network of devices, such as a mesh network formed by autonomous vehicles.

According to various implementations, the autonomous driving system 100 of FIG. 1 functions to enable an autonomous vehicle 110 to modify and/or set a driving behavior in response to parameters set by vehicle passengers (e.g., via a passenger interface) and/or other interested parties (e.g., via a vehicle coordinator or a remote expert interface). Driving behavior of an autonomous vehicle may be modified according to explicit input or feedback (e.g., a passenger specifying a maximum speed or a relative comfort level), implicit input or feedback (e.g., a passenger's heart rate), or any other suitable data or manner of communicating driving behavior preferences.

The autonomous vehicle 110 is preferably a fully autonomous automobile, but may additionally or alternatively be any semi-autonomous or fully autonomous vehicle. In various examples, the autonomous vehicle 110 is a boat, an unmanned aerial vehicle, a driverless car, a golf cart, a truck, a van, a recreational vehicle, a train, a tram, a three-wheeled vehicle, or a scooter. Additionally, or alternatively, the autonomous vehicles may be vehicles that switch between a semi-autonomous state and a fully autonomous state and thus, some autonomous vehicles may have attributes of both a semi-autonomous vehicle and a fully autonomous vehicle depending on the state of the vehicle.

In various implementations, the autonomous vehicle 110 includes a throttle interface that controls an engine throttle, motor speed (e.g., rotational speed of electric motor), or any other movement-enabling mechanism. In various implementations, the autonomous vehicle 110 includes a brake interface that controls brakes of the autonomous vehicle 110 and controls any other movement-retarding mechanism of the autonomous vehicle 110. In various implementations, the autonomous vehicle 110 includes a steering interface that controls steering of the autonomous vehicle 110. In one example, the steering interface changes the angle of wheels of the autonomous vehicle. In some examples, the autonomous vehicle 110 includes a detection and disinfection interface for detecting microbes in and/or on the vehicle and disinfecting one or more portions of the interior and/or exterior of the autonomous vehicle. The autonomous vehicle 110 may additionally or alternatively include interfaces for control of any other vehicle functions, for example, windshield wipers, headlights, turn indicators, air conditioning, etc.

Example Method for Microbe Detection and Disinfection

Figure 2:
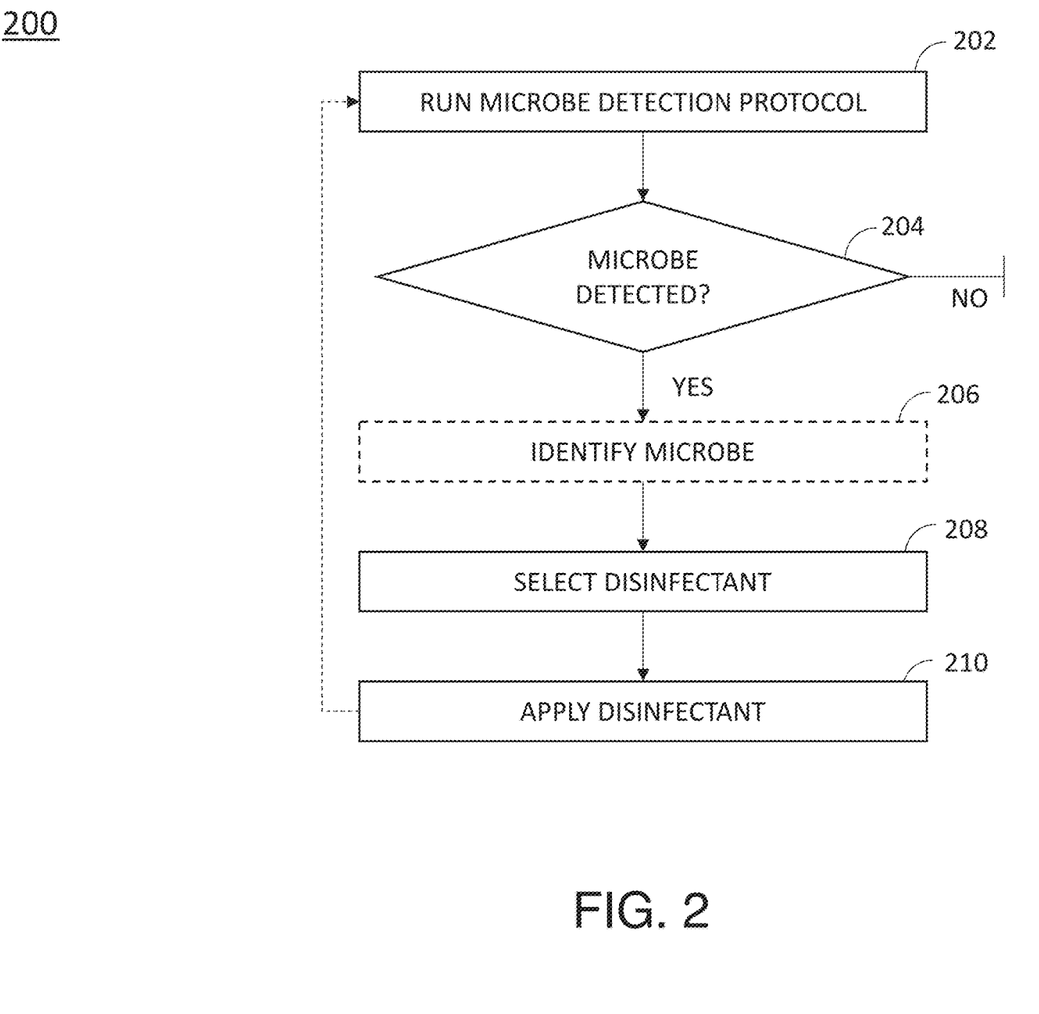
FIG. 2 is a diagram illustrating a method for detecting one or more microbes in an autonomous vehicle and disinfecting the autonomous vehicle, according to various embodiments of the present disclosure.

FIG. 2 is a diagram illustrating a method 200 for detecting one or more microbes in an autonomous vehicle and disinfecting the autonomous vehicle, according to various embodiments of the invention. At step 202, a microbe detection procedure is performed. In various examples, the microbe detection procedure includes detecting microbes within a vehicle. In some examples, the microbe detection procedure includes detecting microbes on a vehicle. The microbe detection procedure can also include detecting microbes close to the vehicle.

There are many possible ways to detect microbes in/on an autonomous vehicle. In some implementations, lights are positioned within the autonomous vehicle that can emit selected light wavelengths. When selected light wavelengths are emitted, the emitted light waves hit various surfaces and the light waves are reflected back to cameras within the vehicle. The light reflects differently based on the shape it reflects off. Reflected wavelengths are analyzed and compared with known signatures of microbes.

In some implementations, a solution is sprayed in the interior of the vehicle via an automated system that includes multiple sprayer nozzles positioned inside the vehicle. In some examples, the solution is a chemical solution, and in some examples, the solution is a luminescent chemical solution. In various implementations, the chemical solution is sprayed throughout the interior of the vehicle. In some examples, the solution is sprayed in specific locations in the vehicle. The specific locations may include "high touch" areas, such as door handles, seat belt buckles, and window controls. In some implementations, a chemical solution is sprayed on the exterior of the vehicle via an automated system that includes one or more sprayer nozzles positioned on the exterior of the vehicle. The solution can reveal the presence of microbes and/or fingerprints. In some examples, the solution is a luminescent chemical solution and, when UV light is emitted after the luminescent chemical solution is applied, the UV light reveals the presence of microbes and/or fingerprints. Cameras in the vehicle capture images of the microbes and/or fingerprints that are revealed by the UV light. Image processing, for example by the onboard computer, can be used for detection of microbes and/or fingerprints.

In some implementations, sensors in the autonomous vehicle are used to detect passenger behavior that may indicate illness, such as coughing, sneezing, nose-blowing, and/or vomiting. In some examples, software determines whether the amount of the passenger behavior(s) exceeds a threshold of what is considered typical behavior. Coughing, sneezing, nose-blowing, and/or other behavior that exceeds the selected threshold can be flagged for potentially introducing microbes in and on the vehicle. Similarly, in some implementations, sensors in the autonomous vehicle are used to detect passenger body temperature. Software determines whether the passenger body temperature exceeds a threshold of what is considered typical body temperature. A high passenger body temperature can be flagged for potentially introducing microbes in and on the vehicle. In various implementations, if a passenger's behavior or body temperature is flagged, this is used as an indication of microbes being present in the vehicle.

At step 204, it is determined whether there are microbes present in the vehicle. As described above, microbe detection systems can indicate the presence of microbes. Similarly, and/or passenger behavior and/or body temperature as detected by vehicle sensors can indicate the presence of microbes. If it is determined that microbes are present, the method proceeds to step 206. If it is determined at step 204 that there are no microbes (or the likelihood and/or amount of microbes does not exceed a selected threshold), the method 200 ends at step 204.

Optionally, at step 206, detected microbes are identified. In some implementations, as discussed above, selected light wavelengths are emitted and the reflections are used to detect microbes. Since light at the emitted wavelengths reflects differently based on the shape it reflects off, reflected wavelengths can be analyzed and compared with known signatures of microbes. An algorithm compares the wavelengths of reflected light to the signatures of various microbes, such as *E. coli, salmonella*, norovirus, hepatitis A, *listeria*, and coronavirus. The algorithm identifies the species of the detected microbe(s) based on the received reflected light.

At step 208, one or more disinfectants (and/or disinfecting methods) is selected for application to the autonomous vehicle. Various disinfectants can be more or less effective against specific microbes. For example, some disinfectants are more effective against viruses than bacteria, and other disinfectants are more effective against bacteria than viruses. In some examples, the microbes are identified, and the disinfectant and/or disinfecting method is selected based on the identification of the microbes. In other examples, the disinfectant and/or disinfecting method is selected based on the length of time it takes for application of the disinfectant and/or completion of the disinfecting method. In other examples, the disinfectant and/or disinfecting method is selected based on autonomous vehicle resources. For instance, the autonomous vehicle reservoir for a selected disinfectant solution may be empty, and thus a different disinfectant or disinfecting method is selected.

One disinfection method includes a distribution of a disinfecting solution. In some implementations, a disinfecting solution is sprayed in the interior of the autonomous vehicle via an automated system that includes multiple sprayer nozzles positioned inside the vehicle. In some examples, the disinfecting solution is sprayed throughout the interior of the vehicle, creating a fog within the vehicle. In some examples, the disinfecting solution is sprayed in specific locations in the vehicle. In some implementations, a disinfecting solution is sprayed on the exterior of the vehicle via an automated system that includes one or more sprayer nozzles positioned on the exterior of the vehicle. In some examples, multiple disinfecting solutions are sprayed in/on the vehicle sequentially and/or simultaneously.

In various examples, a sprayer system is configured for application of multiple solutions through the system. The sprayer system can be connected to multiple different reservoirs of solutions. In various examples, the reservoirs include a reservoir for a detection solution and a reservoir for an antimicrobial solution. In some examples, the reservoirs include multiple reservoirs for different antimicrobial solutions, such as, for instance, an anti-viral solution and an anti-bacterial solution. In some examples, the reservoirs include a reservoir for a protective coating solution and reservoirs for one or more deodorizing solutions. In some implementations, levels of fluids in solution reservoirs are monitored by the onboard computer. Information about the levels of a solution in a reservoir and the frequency of use of the solution can be used to trigger replenishment during the vehicle's regular inspection schedule. When a level of a solution in a reservoir level drops below a certain level, it is flagged for refilling when the autonomous vehicle returns to a service center. In some examples, an autonomous vehicle has a modular replenishment system, and individual solutions are replaced based on usage.

In some implementations, as discussed in greater detail below, the autonomous vehicle is part of a fleet of autonomous vehicles, and fleet data is used to measure fleet-wide levels of microbes and determine an appropriate array of disinfectants to carry on each vehicle for disinfection. In some examples, fleet data is used to determine effectiveness of various disinfectants over selected time periods and/or in selected areas, and disinfectant solutions are replaced with different, more effective, disinfectant solutions.

In some implementations, the sprayer system first applies a disinfecting spray and then applies a protective solution. The protective solution may protect vehicle surfaces from harboring microbes. In some instances, the sprayer system optionally applies a deodorizer. In some instances, the sprayer system applies a selected scent to the vehicle. The selected scent can be passenger selected. In some examples, the sprayer system is used to spray a microbe detection solution and also used to spray a disinfection solution.

Another disinfection method is thermal disinfection. In some examples, thermal disinfection includes heating the vehicle to a selected temperature, wherein the selected temperature is high enough to eradicate microbes. In some examples, thermal disinfection includes heating selected areas of the vehicle to a selected temperature to kill microbes. The selected areas may include "high touch" areas, such as door handles, window controls, and/or seatbelt buckles.

Another disinfection method that can be used is UV light disinfection. Selected UV wavelengths kill microbes, for example UVC light. In some examples, UV light sources are positioned such that the emitted UV light disinfects the interior of the autonomous vehicle. In some examples, UV light sources are positioned such that emitted UV light disinfects selected areas of the vehicle. The UV light sources can be fixed and/or motorized. The selected areas for disinfection may include "high touch" areas, such as door handles, window controls, and/or seatbelt buckles. In some examples, UV light sources are positioned such that emitted UV light disinfects areas on the exterior of the vehicle. In various implementations, the UV light disinfection system first ensures that no passengers are present in the vehicle before emitted UV light. In some examples, the windows of the autonomous vehicle are tinted to prevent emission of UV light outside the vehicle. In some examples, the sensors in the autonomous vehicle sensor system check for the presence of people or animals outside the vehicle before emitting UV light. In some instances, the presence of people and/or animals within a certain distance from the autonomous vehicle (outside the vehicle) disables UV light emission.

In some implementations, UVC light is integrated into the HVAC system to disinfect the air that filters through the HVAC system. In some examples, the HVAC system is configured to adjust air flow such that if a passenger coughs or sneezes, the air flows away from other passengers. In some examples, the autonomous vehicle includes an ozone system for disinfection of the vehicle. In some examples, an ozone system is used to remove scents and/or odors from the vehicle.

At step 210, the disinfecting is performed according to the system and method selected at step 208.

Example Method for Microbe Identification and Disinfection

Figure 3:
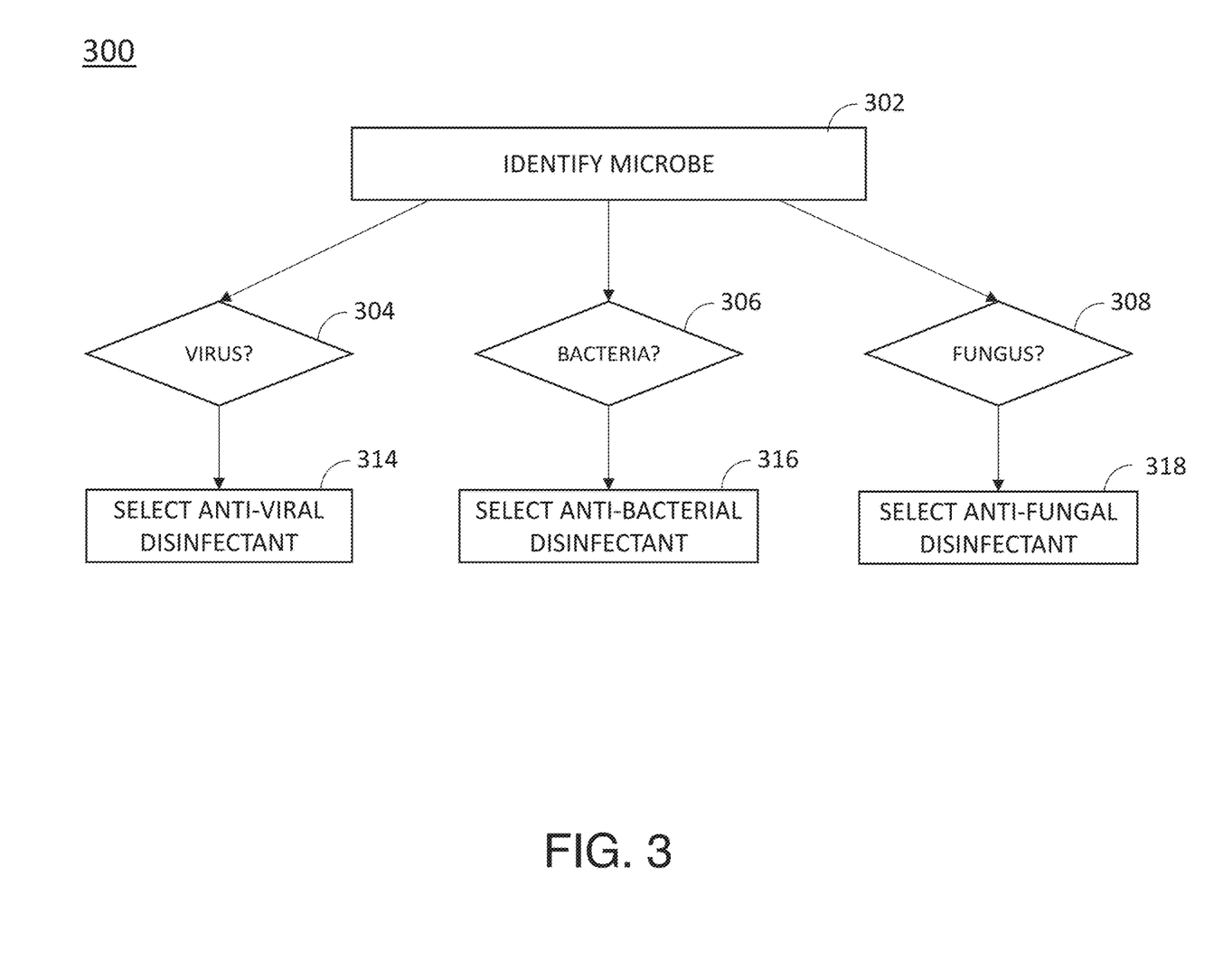
FIG. 3 is a diagram illustrating a method for identifying one or more microbes in an autonomous vehicle, according to various embodiments of the present disclosure.

FIG. 3 is a diagram illustrating a method 300 for identifying one or more microbes in an autonomous vehicle and selecting a disinfectant, according to various embodiments of the invention. At step 302, detected microbes are identified. Any selected method can be used for microbe identification. In some implementations, as discussed above, selected light wavelengths are emitted and the reflections are used to detect microbes. The emitted wavelengths of light reflect differently based on the shape the light reflects off. Reflected wavelengths are received at an identification unit, and the received reflected wavelengths are analyzed and compared with known signatures of microbes for species identification. An algorithm compares the wavelengths of reflected light to the signatures of various microbes, such as *E. coli, salmonella*, norovirus, hepatitis A, *listeria*, coronavirus, and influenza. In other implementations, imaging techniques are used to capture and magnify images of microbes for identification.

From step 302, the method proceeds to steps 304, 306, and 308. At step 304, it is determined whether detected microbes include one or more viruses. If a virus is detected, an anti-viral disinfectant is selected at step 314. At step 306, it is determined whether detected microbes include one or more bacteria. If bacteria are detected, an anti-bacterial disinfectant is selected at step 316. At step 308, it is determined whether detected microbes include one or more fungi. If a fungus is detected, an anti-fungal disinfectant is selected at step 318.

In various implementations, two or more different species of microbes are detected in steps 304, 306, and 308. Thus, at steps 314, 316, and 318, the disinfectant selected can depend on the various species of microbes identified. In one example, viruses and bacteria are identified, and a disinfectant is selected that eliminates both viruses and bacteria. In another example, viruses and fungi are identified, and a disinfectant is selected that eliminates both viruses and fungi. In another example, bacteria and fungi are identified, and a disinfectant is selected that eliminates both bacteria and fungi. In a further examples, viruses, bacteria, and fungi are identified, and a disinfectant is selected that eliminates viruses, bacteria, and fungi. In some implementations, more than one disinfectant and/or disinfecting method is selected.

In various implementations, selecting a disinfectant at steps 314, 316, and 318 includes selecting a disinfecting method and/or system. In various examples, selecting a disinfectant includes one or more of selecting a UV light disinfecting method, a chemical spray disinfecting method, and a thermal disinfecting method. The chemical spray disinfecting method can include a fog emitted throughout the vehicle and it can include a targeted liquid spray directed at one or more specific locations.

In some implementations, different disinfectants are used on different portions of the autonomous vehicle. The disinfectant selected for each of various parts of the autonomous vehicle depends on the type of microbe identified in the selected part of the autonomous vehicle. In one example, microbes on a first seatbelt buckle are identified as virus microbes, and the first seatbelt buckle is treated with an antiviral disinfectant, while microbes on a second seatbelt buckle are identified as bacterial microbes, and the second seatbelt buckle is treated with an antibacterial disinfectant.

In some examples, the cost of running a disinfecting method is considered in selecting a disinfecting method, with a goal of minimizing cost. In some examples, the amount of time a disinfecting method takes is considered in selecting a disinfecting method. For instance, the time may be optimized to complete disinfecting before the autonomous vehicle picks up another passenger.

Example Method for Fleet Management Including Disinfection

Figure 4:
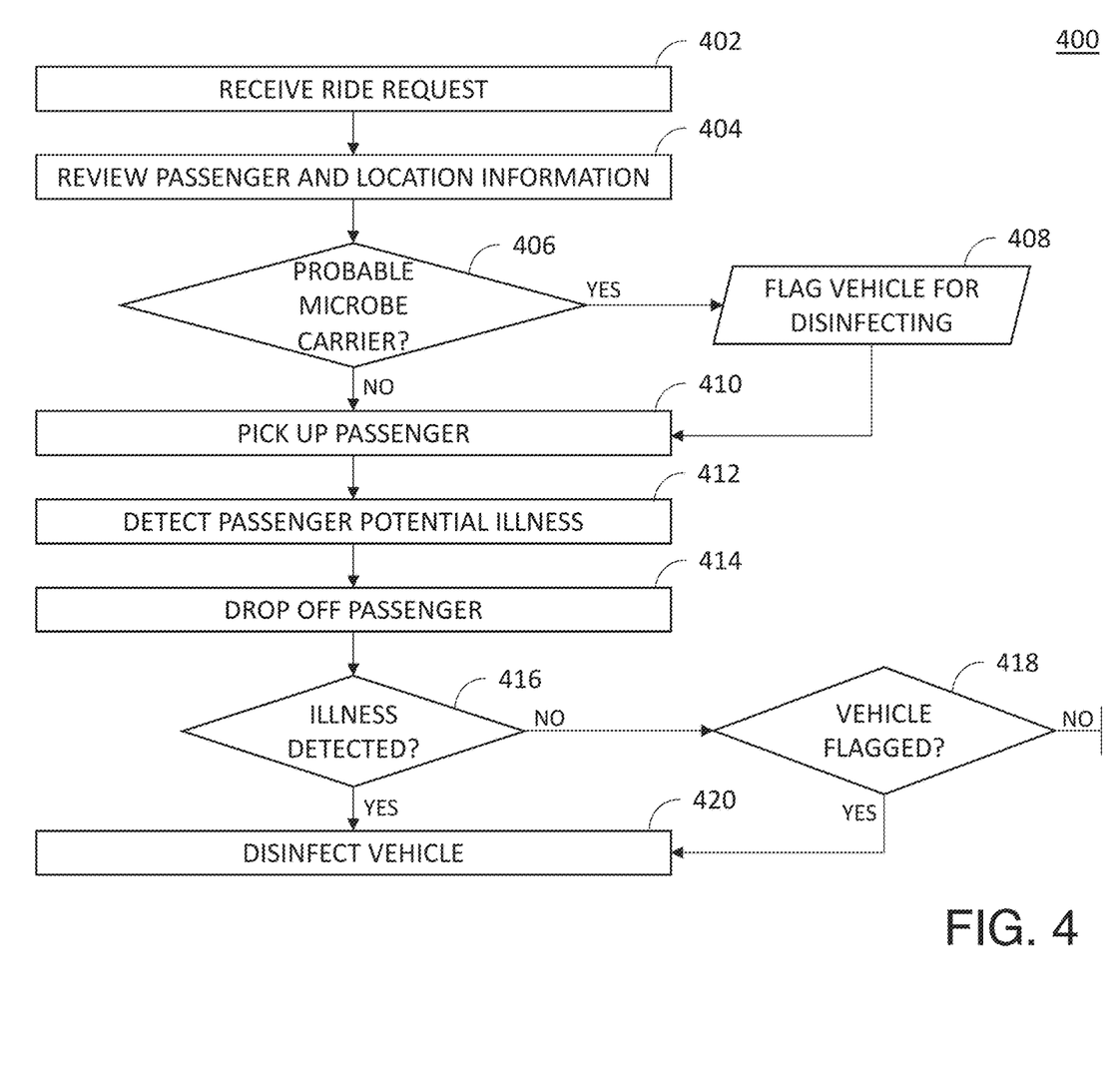
FIG. 4 is a diagram illustrating a method for managing disinfecting of autonomous vehicles in a fleet, according to various embodiments of the present disclosure.

FIG. 4 is a diagram illustrating a method 400 for managing disinfecting of autonomous vehicles in a fleet, according to various embodiments of the invention. At step 402, a ride request is received at a routing coordinator. At step 404, a database is reviewed for passenger information and location information. Passenger information includes previous rides and previous ride locations, and may include any previously detected passenger health data and/or detected microbes in an autonomous vehicle following occupancy by the passenger. In various examples, passengers are notified before any passenger information is stored. In some examples, passengers can adjust personal privacy settings, such that passengers can determine what personal information is stored as passenger information. Location information may include government, agency, or other available health information, such as number of cases of an identified virus or flu in a particular location. The location may include an identified neighborhood (e.g., zip code, town, or city), and it may include a selected radius around the pick-up location.

Based on the passenger information and the location information gathered at step 404, at step 406, it is determined whether the passenger is a probable microbe carrier. At step 406, there may be a specific microbe that is of concern. For example, if there is an outbreak of a specific disease, virus, and/or flu, indications that the passenger may be carrying the microbes causing the outbreak may be specifically considered at step 406. The determination of whether the passenger is a probable microbe carrier at step 406 may be based on a number of factors, including, for example, previously collected passenger health data (such as temperature, trips to the doctor, etc.), health-related questions the passenger answers (e.g., following the ride request), the pick-up location, the location of the passenger's home, and pick-up and drop-off locations of previous rides. Location information may be checked for locations of outbreaks to determine whether the passenger is a high risk of being a microbe carrier. If it is determined that the passenger is a probable microbe carrier, at step 408, the autonomous vehicle is flagged for disinfecting following the ride. The method then proceeds to step 410, picking up the passenger. If it is determined at step 406 that the passenger is not a probable microbe carrier, the vehicle is not flagged, and the method 400 proceeds directly to step 410, picking up the passenger.

At step 412, after the passenger has been picked up, it is determined whether the passenger is potentially currently ill. Current illness determination can be based on passenger body temperature, as detected using sensors inside the autonomous vehicle. Current illness determination can be based on detection of persistent coughing, sneezing, nose-blowing, vomiting, and/or other symptoms of illness. After the passenger is dropped off at step 414, it is determined at step 416 whether symptoms of illness were detected. If symptoms of illness were detected, the method proceeds to step 420 and the vehicle is disinfected. If symptoms of illness were not detected, the method 400 proceeds to step 418, and it is determined whether the vehicle was flagged for disinfecting following the ride. If the vehicle was flagged for disinfecting, the method 400 proceeds to stop 420 and the vehicle is disinfected. In some implementations, if no illness was detected and the vehicle was not flagged, the vehicle proceeds to run a microbe detection protocol to determine whether to disinfect the vehicle, such as the method 200 described with respect to FIG. 2.

In some implementations, different vehicles in the fleet of vehicles use different disinfectants, and data is gathered on the effectiveness of the various disinfectants at during various time periods. In various examples, data is gathered on the effectiveness of the various disinfectants on eliminating microbes and data is gathered on the effectiveness of the various disinfectants on sustaining a microbe-free environment. In particular, in one example, data is gathered on the amount and/or percentage of microbes eliminated following the use of various disinfectants. In another example, to evaluate effectiveness of the various disinfectants in sustaining a microbe-free environment, data is gathered on the amount and/or percentage of new microbes detected in the environment after a selected period of time and/or after a selected event. In another example, to evaluate effectiveness of the various disinfectants in sustaining microbe-free surfaces, data is gathered on the amount and/or percentage of new microbes detected on treated surfaces after a selected period of time and/or after a selected event. Different disinfectants can include different disinfecting methods. In various implementations, gathered data is sent to a central computing service for collection and evaluation.

In some implementations, fleet data is used to measure fleet-wide levels of microbes and determine the appropriate array of disinfectants to carry on each vehicle for disinfection. In one example, an autonomous vehicle has a first reservoir with a first disinfectant installed and a second reservoir with a second disinfectant installed. Fleet data indicates that the first disinfectant is preferable to the second disinfectant, and the second disinfectant is replaced with first disinfectant, such that both the first and second reservoirs contain the first disinfectant. According to some advantages, fleet data can be used to leverage trends in a specific market and/or area and deliver more effective disinfection across the fleet. Furthermore, leveraging trends in specific markets and/or areas can help minimize operating expenses.

In some implementations, a passenger can request disinfection of a vehicle when submitting a ride request. If the passenger submits a request for disinfection, the automatic vehicle is disinfected before passenger pick up. In some examples, the passenger is charged a fee for the disinfection request.

Example Fleet Management System

Figure 5:
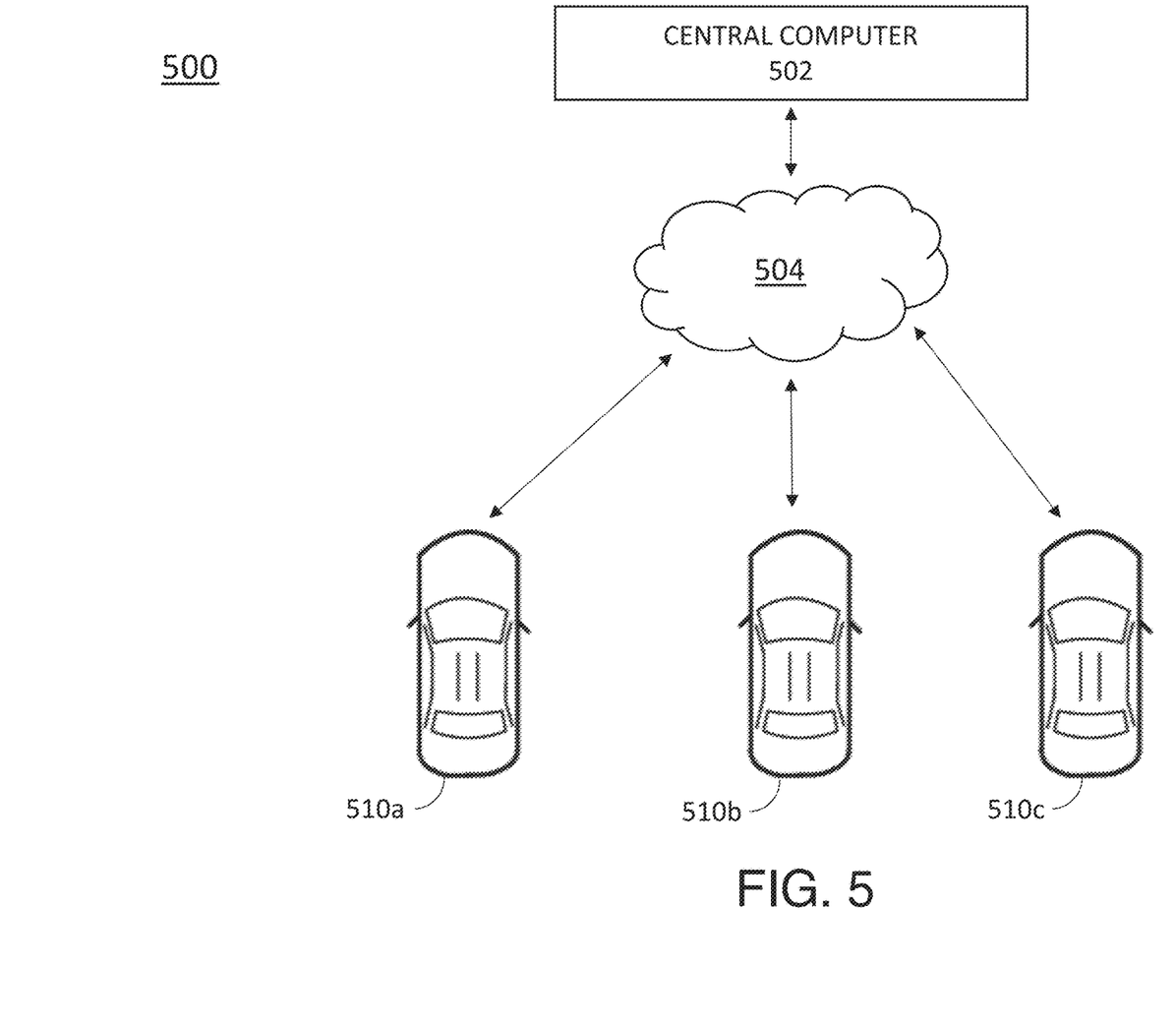
FIG. 5 is a diagram illustrating a fleet of autonomous vehicles in communication with a central computer, according to some embodiments of the present disclosure.

FIG. 5 is a diagram illustrating a fleet of autonomous vehicles 510a-510c in communication with a central computer 502, according to some embodiments of the disclosure. As shown in FIG. 5, the vehicles 510a-510c communicate wirelessly with a cloud 504 and a central computer 502. The central computer 502 includes a routing coordinator and a database of information from the vehicles 510a-510c in the fleet. Autonomous vehicle fleet routing refers to the routing of multiple vehicles in a fleet. In some implementations, autonomous vehicles communicate directly with each other.

When a ride request is received from a passenger, the routing coordinator selects an autonomous vehicle 510a-510c to fulfill the ride request, and generates a route for the autonomous vehicle 510a-510c. The generated route includes a route from the autonomous vehicle's present location to the pick-up location, and a route from the pick-up location to the final destination. In various examples, the time to arrive at the pick-up location is adjusted to add time to run a microbe detection protocol and/or time for disinfecting the vehicle before arrival, as discussed above. In some examples, the microbe detection protocol and/or disinfecting occur en route to the pick-up location and no extra time is added.

Each vehicle 510a-510c in the fleet of vehicles communicates with a routing coordinator. Information gathered by various autonomous vehicles 510a-510c in the fleet can be saved and used to generate information for future routing and/or disinfecting determinations. For example, sensor data can be used to generate route determination parameters. In another example, sensor data can be used to detect and record illness indications of the passenger. In another example, sensor data can be used to detect and record microbes in the vehicle following passenger use. In general, the information collected from the vehicles in the fleet can be used to update passenger information in a passenger account database, as well as for route generation or to modify existing routes.

In some examples, the routing coordinator collects and processes position data from multiple autonomous vehicles in real-time to avoid traffic and generate a fastest-time route for each autonomous vehicle. In some implementations, the routing coordinator uses collected position data to generate a best route for an autonomous vehicle in view of one or more travelling preferences and/or routing goals.

According to various implementations, a set of parameters can be established that determine which metrics are considered (and to what extent) in determining routes or route modifications. Generally, a routing goal refers to, but is not limited to, one or more desired attributes of a routing plan indicated by at least one of an administrator of a routing server and a user of the autonomous vehicle. The desired attributes may relate to a desired duration of a route plan, a comfort level of the route plan, a vehicle type for a route plan, and the like. For example, a routing goal may include time of an individual trip for an individual autonomous vehicle be minimized, subject to other constraints. As another example, a routing goal may be that comfort of an individual trip for an autonomous vehicle be enhanced or maximized, subject to other constraints.

Routing goals may be specific or general in terms of both the vehicles they are applied to and over what timeframe they are applied. As an example of routing goal specificity in vehicles, a routing goal may apply only to a specific vehicle, or to all vehicles in a specific region, or to all vehicles of a specific type, etc. Routing goal timeframe may affect both when the goal is applied (e.g., some goals may be 'active' only during set times) and how the goal is evaluated (e.g., for a longer-term goal, it may be acceptable to make some decisions that do not optimize for the goal in the short term, but may aid the goal in the long term). Likewise, routing vehicle specificity may also affect how the goal is evaluated; e.g., decisions not optimizing for a goal may be acceptable for some vehicles if the decisions aid optimization of the goal across an entire fleet of vehicles. Routing goals may take into consideration other fleet-provided services such as disinfection of vehicles.

Some examples of routing goals include goals involving trip duration (either per trip, or average trip duration across some set of vehicles and/or times), physics, laws, and/or company policies (e.g., adjusting routes chosen by users that end in lakes or the middle of intersections, refusing to take routes on highways, etc.), distance, velocity (e.g., max., min., average), source/destination (e.g., it may be optimal for vehicles to start/end up in a certain place such as in a pre-approved parking space or charging station), intended arrival time (e.g., when a user wants to arrive at a destination), duty cycle (e.g., how often a car is on an active trip vs. idle), energy consumption (e.g., gasoline or electrical energy), maintenance cost (e.g., estimated wear and tear), money earned (e.g., for vehicles used for ridesharing), person-distance (e.g., the number of people moved multiplied by the distance moved), occupancy percentage, higher confidence of arrival time, user-defined routes or waypoints, fuel status (e.g., how charged a battery is, how much gas is in the tank), passenger satisfaction (e.g., meeting goals set by or set for a passenger) or comfort goals, environmental impact, passenger safety, pedestrian health, toll cost, etc. In examples where vehicle demand is important, routing goals may include attempting to address or meet vehicle demand.

Routing goals may be combined in any manner to form composite routing goals; for example, a composite routing goal may attempt to optimize a performance metric that takes as input trip duration, rideshare revenue, and energy usage and also, optimize a comfort metric. The components or inputs of a composite routing goal may be weighted differently and based on one or more routing coordinator directives and/or passenger preferences.

Likewise, routing goals may be prioritized or weighted in any manner. For example, a set of routing goals may be prioritized in one environment, while another set may be prioritized in a second environment. As a second example, a set of routing goals may be prioritized until the set reaches threshold values, after which point a second set of routing goals take priority. Routing goals and routing goal priorities may be set by any suitable source (e.g., an autonomous vehicle routing platform, an autonomous vehicle passenger).

In some examples, routing goals include keeping a subset of vehicles within a selected area. In other examples, routing goals include using a subset of vehicles for rides to and from health care facilities, such as hospitals. In some instances, autonomous vehicles that drive to and/or from a health care facilities are disinfected following the drive and before beginning another route.

In some implementations, the central computer tracks microbe detection across the fleet of vehicles. Microbe detection data can be used to determine areas with high levels of microbes, areas with increasing numbers of microbes, and levels of a specific type or species of microbe.

The routing coordinator uses maps select an autonomous vehicle from the fleet to fulfill a ride request. In some implementations, the routing coordinator sends the selected autonomous vehicle the ride request details, including pick-up location and destination location, and an onboard computer on the selected autonomous vehicle generates a route and navigates to the destination and/or any intermediate stop. While the passenger is in the vehicle, sensors in the vehicle may continuously evaluate the passenger for health-related (and illness-related) behaviors. In some implementations, the routing coordinator in the central computing system 502 generates a route for each selected autonomous vehicle 510*a*-510*c*, and the routing coordinator considered adding additional time following a ride for vehicle microbe detection and/or disinfection.

Example of Fleet Management for Disinfecting

Figure 6:
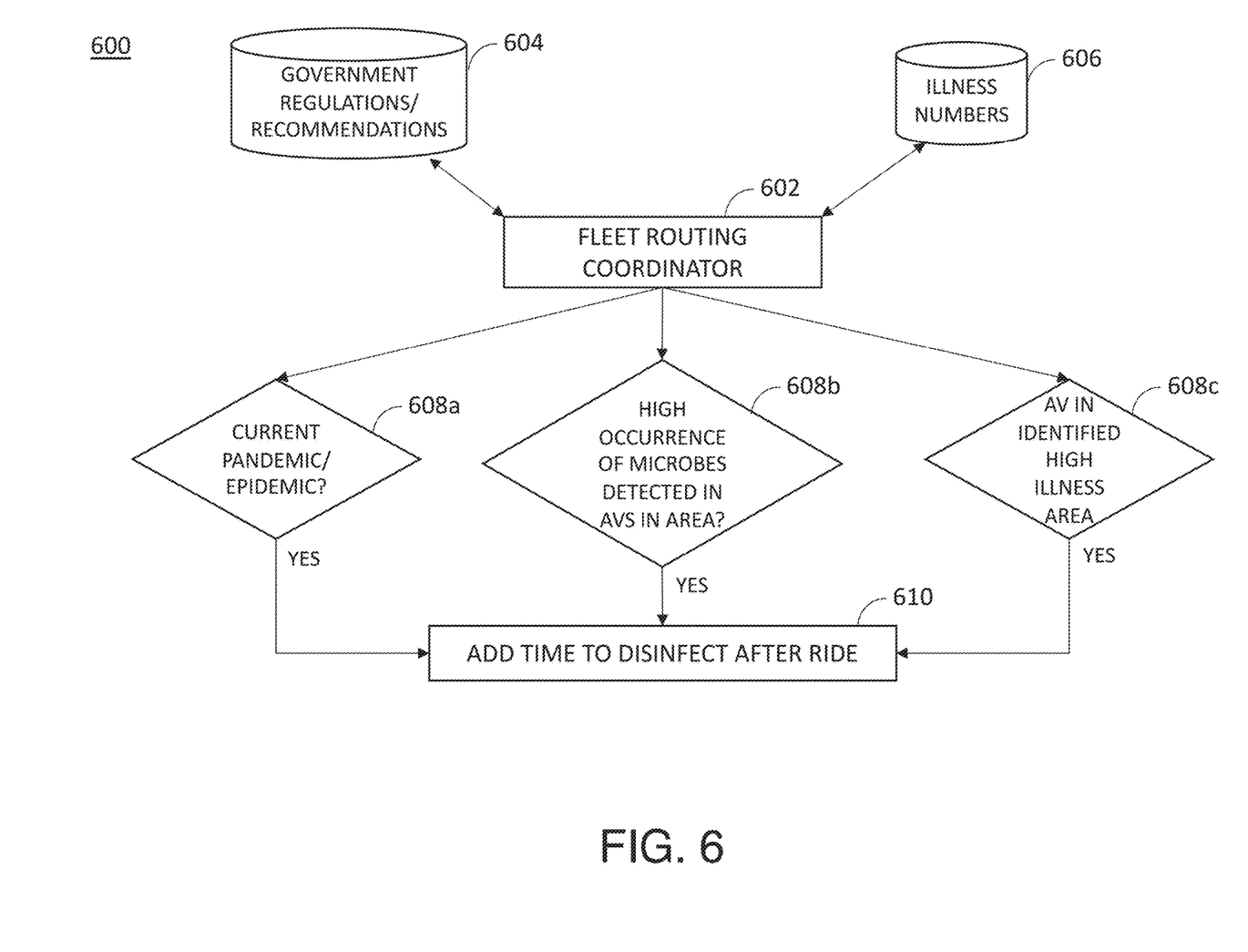
FIG. 6 is a diagram illustrating a method of adjusting automated disinfecting schedules for autonomous vehicles in a fleet based on local data and health recommendations, according to some embodiments of the present disclosure.

FIG. 6 is a diagram illustrating a method 600 of adjusting automated disinfecting schedules for autonomous vehicles in a fleet based on local data and health recommendations, according to some embodiments of the disclosure. In particular, a fleet routing coordinator 602 uses information such as government regulations 604 and illness numbers 606 to determine whether to add disinfecting time to one or more autonomous vehicles in the fleet following a ride. The routing coordinator 602 receives up-to-date information from government agencies about health recommendations and regulations. The routing coordinator 602 may also consult other databases for health recommendations. The routing coordinator 602 also receives up-to-date illness numbers 606 to identify localized areas with high illness numbers. The localized areas can be any size, including, for example, a geofenced area of several blocks, a zip code, a city, a county, and a state.

The routing coordinator 602 uses the information to determine when a microbe detection and/or disinfecting protocol is run. In various examples, the routing coordinator 602 determines at step 608*a* whether there is a current pandemic or epidemic in the area where a particular autonomous vehicle, or fleet of autonomous vehicles, is driving. If there is a current pandemic or epidemic, the routing coordinator adds time to the end of each vehicle's route for a microbe detection and/or disinfection protocol. The time may overlap with the time for the vehicle to drive to its next destination, since the microbe detection and/or disinfection can occur while the vehicle is driving. In another example, the routing coordinator 602 determines at step 608*b* whether there has been a high occurrence of microbes detected in autonomous vehicles in an area where a particular autonomous vehicle, or fleet of autonomous vehicles, is driving. If there has been a high occurrence of microbes, the routing coordinator adds time to the end of each vehicle's route for a microbe detection and/or disinfection protocol. In a further example, the routing coordinator 602 determines at step 608*c* whether the area where a particular autonomous vehicle, or fleet of autonomous vehicles, is driving is an identified high-illness area. If an autonomous vehicle is operating in a high illness area, the routing coordinator includes time to the end of the vehicle's route for a microbe detection and/or disinfection protocol. The time for microbe detection/disinfection may occur partially and/or entirely within the time during which the vehicle drives to its next destination.

Example of a Computing System for Ride Requests

Figure 7:
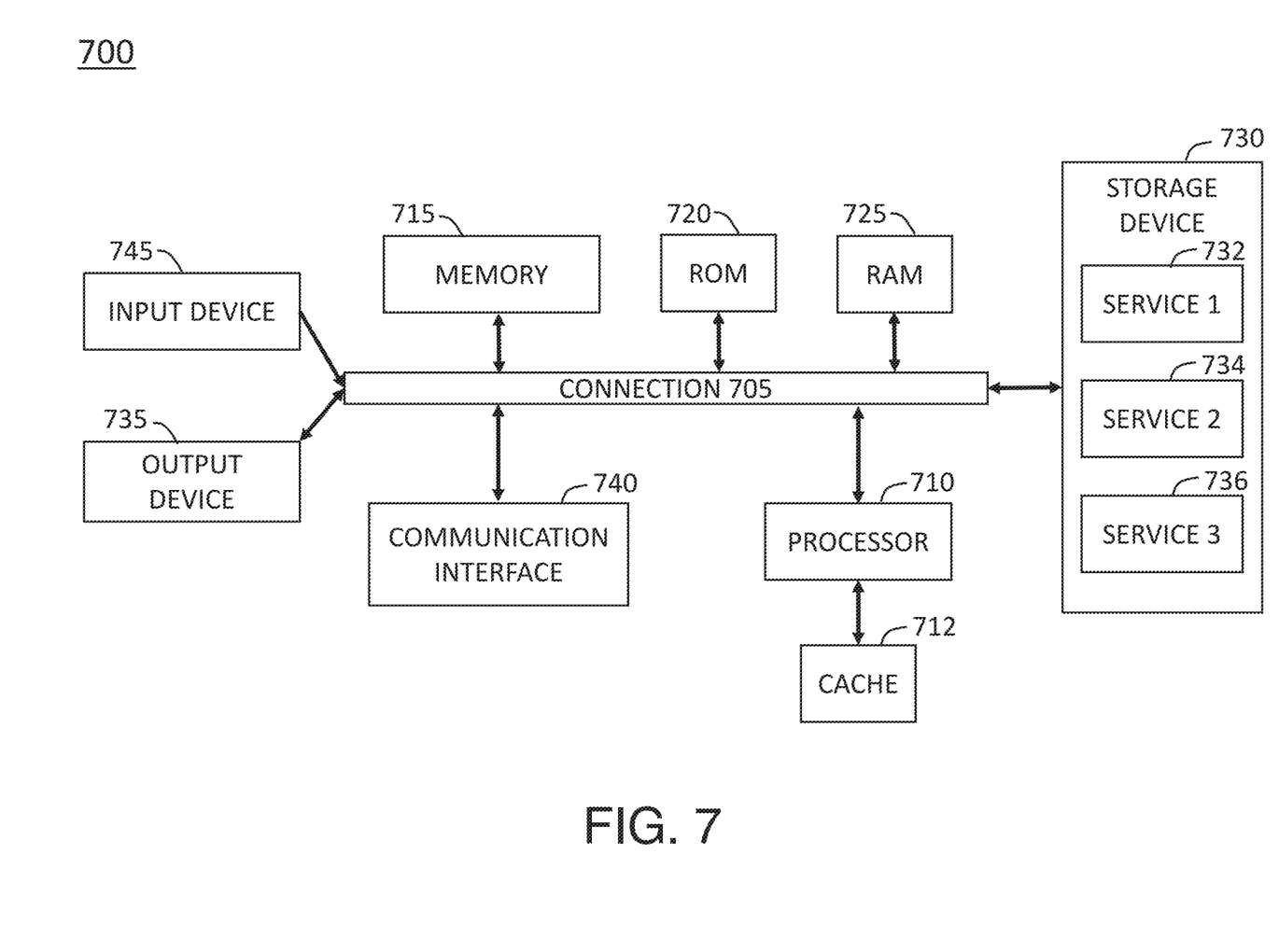
FIG. 7 shows an example embodiment of a system for implementing certain aspects of the present technology.

FIG. 7 shows an example embodiment of a computing system 600 for implementing certain aspects of the present technology. In various examples, the computing system 700 can be any computing device making up the onboard computer 104, the central computing system 502, or any other computing system described herein. The computing system 700 can include any component of a computing system described herein which the components of the system are in communication with each other using connection 705. The connection 705 can be a physical connection via a bus, or a direct connection into processor 710, such as in a chipset architecture. The connection 705 can also be a virtual connection, networked connection, or logical connection.

In some implementations, the computing system 700 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

The example system 700 includes at least one processing unit (CPU or processor) 710 and a connection 705 that couples various system components including system memory 715, such as read-only memory (ROM) 720 and random access memory (RAM) 725 to processor 710. The computing system 700 can include a cache of high-speed memory 712 connected directly with, in close proximity to, or integrated as part of the processor 710.

The processor 710 can include any general-purpose processor and a hardware service or software service, such as services 732, 734, and 736 stored in storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction, the computing system 700 includes an input device 745, which can represent any number of input mechanisms, such as a microphone for speech, a touch-sensitive screen for gesture or graphical input, keyboard, mouse, motion input, speech, etc. The computing system 700 can also include an output device 735, which can be one or more of a number of output mechanisms known to those of skill in the art. In some instances, multimodal systems can enable a user to provide multiple types of input/output to communicate with the computing system 700. The computing system 700 can include a communications interface 740, which can generally govern and manage the user input and system output. There is no restriction on operating on any particular hardware arrangement, and therefore the basic features here may easily be substituted for improved hardware or firmware arrangements as they are developed. In some implementations, input includes input from sensors in the autonomous vehicle.

A storage device 730 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read-only memory (ROM), and/or some combination of these devices.

The storage device 730 can include software services, servers, services, etc., that when the code that defines such software is executed by the processor 710, it causes the system to perform a function. In some embodiments, a hardware service that performs a particular function can include the software component stored in a computer-readable medium in connection with the necessary hardware components, such as a processor 710, a connection 705, an output device 735, etc., to carry out the function.

As discussed above, each vehicle in a fleet of vehicles communicates with a routing coordinator. When a vehicle is flagged for service, the routing coordinator schedules the vehicle for service and routes the vehicle to the service center. When the vehicle is flagged for maintenance, a level of importance or immediacy of the service can be included. As such, service with a low level of immediacy will be scheduled at a convenient time for the vehicle and for the fleet of vehicles to minimize vehicle downtime and to minimize the number of vehicles removed from service at any given time. In some examples, the service is performed as part of a regularly-scheduled service. Service with a high level of immediacy may require removing vehicles from service despite an active need for the vehicles.

Routing goals may be specific or general in terms of both the vehicles they are applied to and over what timeframe they are applied. As an example of routing goal specificity in vehicles, a routing goal may apply only to a specific vehicle, or to all vehicles of a specific type, etc. Routing goal timeframe may affect both when the goal is applied (e.g., urgency of the goal, or, some goals may be 'active' only during set times) and how the goal is evaluated (e.g., for a longer-term goal, it may be acceptable to make some decisions that do not optimize for the goal in the short term, but may aid the goal in the long term). Likewise, routing vehicle specificity may also affect how the goal is evaluated; e.g., decisions not optimizing for a goal may be acceptable for some vehicles if the decisions aid optimization of the goal across an entire fleet of vehicles.

In various implementations, the routing coordinator is a remote server or a distributed computing system connected to the autonomous vehicles via an internet connection. In some implementations, the routing coordinator is any suitable computing system. In some examples, the routing coordinator is a collection of autonomous vehicle computers working as a distributed system.

As described herein, one aspect of the present technology is the gathering and use of data available from various sources to improve quality and experience. The present disclosure contemplates that in some instances, this gathered data may include personal information. The present disclosure contemplates that the entities involved with such personal information respect and value privacy policies and practices.

Select Examples

Example 1 provides a method for automated detection and disinfection of microbes in an autonomous vehicle including autonomously scanning a plurality of identified parts of the autonomous vehicle for microbes, detecting microbes on at least one of the plurality of parts, selecting an automatic disinfecting method based on the microbes, and autonomously disinfecting at least one of the identified parts of the autonomous vehicle, wherein the at least one part includes the microbes.

Example 2 provides a method according to example 1, further including identifying a species of the microbes.

Example 3 provides a method according to one or more of the preceding examples, wherein selecting the disinfecting method includes selecting based on the species of the microbes.

Example 4 provides a method according to one or more of the preceding examples further including selecting a disinfecting solution from a plurality of disinfecting solutions based on the species of the microbes.

Example 5 provides a method according to one or more of the preceding examples wherein selecting the disinfecting method includes selecting at least one of UV light disinfection, targeted distribution of a disinfecting solution, fog distribution of a disinfecting solution, and thermal disinfection.

Example 6 provides a method according to one or more of the preceding examples, further including determining, for each of the plurality of identified parts, whether the microbes are detected.

Example 7 provides a method according to one or more of the preceding examples including detecting the microbes on at least two of the plurality of identified parts, identifying a first species of microbes on a first identified part, and identifying a second species of microbes on a second identified part.

Example 8 provides a method according to one or more of the preceding examples further comprising selecting a first disinfectant for disinfecting the first identified part, and selecting a second disinfectant for disinfecting the second identified part.

Example 9 provides a method according to one or more of the preceding examples wherein disinfecting occurs while the autonomous vehicle is driving.

Example 10 provides a system for automated detection and disinfection of microbes in an autonomous vehicle, comprising a microbe detection unit configured to autonomously perform microbe detection, wherein the microbe detection unit includes a scanning element configured to scan a plurality of identified parts of the autonomous vehicle for microbes, an onboard computer configured to receive scans from the scanning element, and determine whether microbes are detected on each of the plurality of parts, and a disinfection system configured to autonomously disinfect the plurality of parts of the autonomous vehicle.

Example 11 provides a system according to one or more of the preceding examples, further comprising a plurality of storage tanks for storing different disinfecting solutions.

Example 12 provides a system according to one or more of the preceding examples including a plurality of spray elements for emitting the disinfecting solutions, wherein a first spray element is directed at a first part of the autonomous vehicle and a second spray element is directed at a second part of the autonomous vehicle, and wherein a first storage tank is connected to the first spray element and a second storage tank is connected to the second spray element.

Example 13 provides a system according to one or more of the preceding examples wherein the onboard computer is further configured to identify a species of the microbes and select a disinfecting method based on the species of the microbes.

Example 14 provides a system according to one or more of the preceding examples further including ultraviolet (UV) light sources configured to emit UV light on the plurality of identified parts of the autonomous vehicle.

Example 15 provides a system according to one or more of the preceding examples wherein the UV light source is configured to illuminate microbes on the plurality of identified parts of the autonomous vehicle.

Example 16 provides a system according to one or more of the preceding examples, wherein the UV light source is configured to disinfect microbes on the plurality of identified parts of the autonomous vehicle.

Example 17 provides a system according to one or more of the preceding examples, wherein the onboard computer is configured to identify selected parts of the plurality of identified parts having microbes, and the disinfection system is configured to disinfect the selected parts.

Example 18 provides a method for automated identification and disinfection of microbes in an autonomous vehicle, comprising autonomously detecting a plurality of microbes on a part of the autonomous vehicle, identifying a species of the plurality of microbes, selecting a disinfectant based on the species of the plurality of microbes, and autonomously disinfecting at least the part of the autonomous vehicle using the selected disinfectant.

Example 19 provides a method according to one or more of the preceding examples, further comprising spraying chemical solution within the autonomous vehicle and emitting UV light to illuminate the plurality of microbes on the part of the autonomous vehicle.

Example 20 provides a method according to one or more of the preceding examples, wherein identifying the species includes capturing an image of the part of the autonomous vehicle while emitting the UV light, and processing the image.

Example 21 provides a method according to one or more of the preceding examples, wherein selecting the disinfectant includes selecting at least one of UV light disinfection, targeted distribution of a disinfecting solution, fog distribution of a disinfecting solution, and thermal disinfection.

Example 22 provides a method according to one or more of the preceding examples, further comprising contacting a routing coordinator to determine whether to add time for disinfection following a route.

Example 23 provides a system for managing a fleet of autonomous vehicles (AVs) comprising a user interface server configured to receive a request for a ride from a user, the request comprising an origin location and a destination location, a vehicle manager configured to instruct a selected AV of the fleet to drive to the origin location, a microbe detection protocol configured to determine likelihood microbes on the selected AV following the ride and, based on the determination, autonomously disinfect the AV.

Example 24 provides a system according to one or more of the preceding examples, wherein the vehicle manager is configured to add time to an end of the ride for at least one of microbe detection and disinfection.

Variations and Implementations

According to various examples, driving behavior includes any information relating to how an autonomous vehicle drives. For example, driving behavior includes how and when the autonomous vehicle actuates its brakes and its accelerator, and how it steers. In particular, the autonomous vehicle is given a set of instructions (e.g., a route or plan), and the driving behavior determines how the set of instructions is implemented to drive the car to and from various destinations, and, potentially, to stop for passengers or items. Driving behavior may include a description of a controlled operation and movement of an autonomous vehicle and the manner in which the autonomous vehicle applies traffic rules during one or more driving sessions. Driving behavior may additionally or alternatively include any information about how an autonomous vehicle calculates routes (e.g., prioritizing fastest time vs. shortest distance), other autonomous vehicle actuation behavior (e.g., actuation of lights, windshield wipers, traction control settings, etc.) and/or how an autonomous vehicle responds to environmental stimulus (e.g., how an autonomous vehicle behaves if it is raining, or if an animal jumps in front of the vehicle). Some examples of elements that may contribute to driving behavior include acceleration constraints, deceleration constraints, speed constraints, steering constraints, suspension settings, routing preferences (e.g., scenic routes, faster routes, no highways), lighting preferences, "legal ambiguity" conduct (e.g., in a solid-green left turn situation, whether a vehicle pulls out into the intersection or waits at the intersection line), action profiles (e.g., how a vehicle turns, changes lanes, or performs a driving maneuver), and action frequency constraints (e.g., how often a vehicle changes lanes). Additionally, driving behavior includes information relating to whether the autonomous vehicle drives and/or parks.

As will be appreciated by one skilled in the art, aspects of the present disclosure, in particular aspects of a perception system for an autonomous vehicle, described herein, may be embodied in various manners (e.g., as a method, a system, a computer program product, or a computer-readable storage medium). Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The preceding disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Other features and advantages of the disclosure will be apparent from the description and the claims. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

What is claimed is:

1. A system for automated detection and disinfection of microbes in an autonomous vehicle fleet, comprising:
the fleet of autonomous vehicles, each autonomous vehicle comprising:
a microbe detection unit coupled to the respective autonomous vehicle configured to autonomously perform microbe detection, wherein the microbe detection unit includes a scanning element configured to scan a plurality of parts of the respective autonomous vehicle for microbes;
an onboard computer in the respective autonomous vehicle configured to:
receive scans of the plurality of parts of the respective autonomous vehicle from the scanning element, and
determine whether microbes are detected on each of the plurality of parts; and
a disinfection system configured to autonomously disinfect at least one part of the plurality of parts of the respective autonomous vehicle wherein the at least one part includes detected microbes,
wherein the disinfection system is configured to autonomously disinfect for a predetermined time while the respective autonomous vehicle is driving along a route, and
wherein the disinfection system is configured to contact a routing coordinator to determine whether to add time for disinfection following the route; and
a central computer in communication with each autonomous vehicle of the fleet of autonomous vehicles, configured to:
receive microbe detection data from the fleet of autonomous vehicles, and
determine fleet-wide levels of microbes.

2. The system of claim 1, wherein the onboard computer in each respective autonomous vehicle is further configured to identify a species of the microbes and select a disinfecting method based on the species of the microbes.

3. The system of claim 2, wherein the central computer is further configured to receive microbe detection data including identified species of microbes.

4. The system of claim 3, wherein the central computer is further configured to identify a plurality of disinfectants to carry on each vehicle, based on the fleet-wide data including identified species of microbes.

5. The system of claim 4, wherein each respective autonomous vehicle further comprises a plurality of storage tanks for storing the plurality of disinfectants.

6. The system of claim 4, wherein the plurality of disinfectants includes a plurality of disinfecting methods, wherein the disinfecting methods include an ultraviolet (UV) light source configured to emit UV light and spray elements configured to emit a disinfecting solution.

7. A system for automated detection and disinfection of microbes in an autonomous vehicle, comprising:
a microbe detection unit coupled to the autonomous vehicle configured to autonomously perform microbe detection, wherein the microbe detection unit includes a scanning element configured to scan a plurality of parts of the autonomous vehicle for microbes;
an onboard computer in the autonomous vehicle configured to:
receive scans of the plurality of parts of the autonomous vehicle from the scanning element, and
determine whether microbes are detected on each of the plurality of parts; and
a disinfection system configured to autonomously disinfect at least one part of the plurality of parts of the autonomous vehicle wherein the at least one part includes detected microbes,
wherein the disinfection system is configured to autonomously disinfect for a predetermined time while the autonomous vehicle is driving along a route, and
wherein the disinfection system is configured to contact a routing coordinator to determine whether to add time for disinfection following the route.

8. The system of claim 7, further comprising a plurality of storage tanks for storing different disinfecting solutions.

9. The system of claim 8, further comprising a plurality of spray elements coupled to the autonomous vehicle for emitting the disinfecting solutions,
wherein a first spray element is directed at a first part of the autonomous vehicle and a second spray element is directed at a second part of the autonomous vehicle, and
wherein a first storage tank is connected to the first spray element and a second storage tank is connected to the second spray element.

10. The system of claim 7, wherein the onboard computer is further configured to receive fleet data including fleet-wide levels of microbes.

11. The system of claim 7, wherein the onboard computer is further configured to identify a species of the microbes and select a disinfecting method based on the species of the microbes.

12. The system of claim 7, further comprising an ultraviolet (UV) light source configured to emit UV light on the plurality of parts of the autonomous vehicle.

13. The system of claim 12, wherein the UV light source is configured to illuminate microbes on the plurality of parts of the autonomous vehicle.

14. The system of claim 12, wherein the UV light source is configured to disinfect microbes on the plurality of parts of the autonomous vehicle.

15. The system of claim 7, wherein the onboard computer is configured to identify selected parts of the plurality of parts having microbes, and the disinfection system is configured to disinfect the selected parts.

16. A system for automated detection and disinfection of microbes in an autonomous vehicle fleet, comprising:
a plurality of autonomous vehicles, each autonomous vehicle comprising:
a microbe detection unit coupled to the respective autonomous vehicle configured to autonomously perform microbe detection;
an onboard computer in the respective autonomous vehicle configured to:
determine whether microbes are detected on each of the plurality of parts and
identify, if microbes are detected on any part, a species of the microbes detected on the respective part; and
a disinfection system configured to autonomously disinfect at least one part of the plurality of parts of the respective autonomous vehicle wherein the at least one part includes detected microbes,
wherein the disinfection system is configured to autonomously disinfect for a predetermined time while the respective autonomous vehicle is driving along a route, and wherein the disinfection system is configured to contact a routing coordinator to determine whether to add time for disinfection following the route, a central computer in communication with each autonomous vehicle of the plurality of autonomous vehicles, configured to:
receive microbe detection data from the plurality of autonomous vehicles including identified species of microbes, and
identify high levels of microbes across the plurality of autonomous vehicles.

17. The system of claim 16, wherein the onboard computer in each respective autonomous vehicle is further configured to select a disinfecting method based on the species of the microbes.

18. The system of claim 16, wherein the central computer is further configured to identify a plurality of disinfectants to carry on each vehicle, based on the identified species of microbes.

19. The system of claim 18, wherein each respective autonomous vehicle further comprises a plurality of storage tanks for storing the plurality of disinfectants.

20. The system of claim 16, wherein the central computer is further configured to determine levels of each of the identified species of microbes across the plurality of autonomous vehicles.

* * * * *